United States Patent [19]
Pies et al.

[11] Patent Number: 5,523,481
[45] Date of Patent: Jun. 4, 1996

[54] PROCESS FOR THE PREPARATION OF DIALKYL DICARBONATES

[75] Inventors: Michael Pies, Duisburg; Helmut Fiege, Leverkusen; Josef Käsbauer, Wermelskirchen; Gebhard Merz, Krefeld, all of Germany

[73] Assignee: Bayer Aktiengesellschaft, Leverkusen, Germany

[21] Appl. No.: 347,660

[22] Filed: Dec. 1, 1994

[30] Foreign Application Priority Data

Dec. 8, 1993 [DE] Germany ............ 43 41 747.7

[51] Int. Cl.⁶ .................... C07C 51/56; C07C 51/54
[52] U.S. Cl. ............................ 562/894; 562/888
[58] Field of Search ..................... 562/894, 888

[56] References Cited

U.S. PATENT DOCUMENTS 3,326,958  6/1967  Curtius et al. ............... 558/277

FOREIGN PATENT DOCUMENTS 0468404  1/1992  European Pat. Off. .

OTHER PUBLICATIONS

Daniel Plusquellec et al., "A New Synthesis of Carboxylic and Carbonic Acid Anhydrides Using Phase Transfer Reactions", *Tetrathedron*, Bd. 44, No. 9., pp. 2471–2476 1988. *das ganze Dokument*.

Primary Examiner—José G. Dees
Assistant Examiner—Dwayne C. Jones
Attorney, Agent, or Firm—Sprung Horn Kramer & Woods

[57] ABSTRACT

Dialkyl dicarbonates are obtained particularly advantageously from halogenoformic esters by reaction with alkalis in the presence of water-immiscible organic solvents and in the presence of a catalyst, if the catalyst used is benzylalkyldimethylammonium halides. The catalyst is then particularly easy to separate off and to recycle from the reaction mixture.

7 Claims, No Drawings

PROCESS FOR THE PREPARATION OF DIALKYL DICARBONATES

The present invention relates to a process for the preparation of dialkyl dicarbonates by reaction of corresponding chloroformic esters with alkalis in the presence of special catalysts. Dialkyl dicarbonates are used, e.g., as cold sterilants for sterilizing fruit juice beverages and alcohol-free wine. Dialkyl dicarbonates are also termed dialkyl pyrocarbonates.

A process for the preparation of, inter alia, dialkyl dicarbonates has already become known in which chloroformic esters are reacted with aqueous sodium hydroxide solution in the presence of an organic solvent and in the presence of tetra-n-butylammonium chloride or tri-n-caprylmethylammonium chloride as a phase transfer catalyst (see Tetrahedron 44 (9), 2471–2476 (1988)). It is a disadvantage with this process that high amounts of catalysts are required (0.1 equivalent=10 mol %) and that the catalyst can only be recovered and recycled with great difficulty because it collects either in the aqueous or in the organic phase and can only be separated off therefrom with great expense. Recovery and recycling of the catalyst is highly desirable on the one hand for reasons of costs and on the other hand because, otherwise, problems arise with the disposal of catalyst-containing production residues.

A process has now been found for the preparation of dialkyl dicarbonates from the corresponding halogenoformic esters by reaction with alkalis in the presence of water-immiscible organic solvents and in the presence of catalysts, which is characterized in that the catalysts used are benzylalkyldimethylammonium halides.

By means of the process according to the invention, for example, from halogenoformic esters of the formula (I)

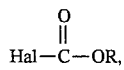

in which

Hal represents halogen, in particular chlorine, and

R represents a straight-chain or branched $C_1$–$C_{20}$-alkyl radical, dialkyl dicarbonates of the formula (II) can be prepared

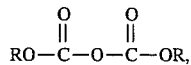

in which

R has the meaning given in formula (I).

In the formulae (I) and (II), R preferably represents a $C_1$–$C_8$-alkyl radical, and the alkyl group C atom bound to the oxygen preferably has at least one further hydrogen atom. In particular, R represents methyl, ethyl, n-propyl, i-propyl, n-butyl or i-butyl.

Alkalis which are useful are, in particular, alkali metal hydroxides such as sodium hydroxide and potassium hydroxide which are preferably used in the form of aqueous solutions. For example, 5 to 30% strength by weight aqueous alkali metal hydroxide solutions can be used. 10 to 20% strength by weight solutions are preferred.

The alkalis can be used, for example, in amounts of 80 to 120 mol %, based on halogenoformic esters used. This amount is preferably in the range from 95 to 105 mol %.

Water-immiscible organic solvents which are useful are, for example, aromatic hydrocarbons, chlorinated hydrocarbons and water-immiscible ethers. Toluene, xylene, methylene chloride and diethyl ether are preferred, in particular toluene and methylene chloride.

The water-immiscible organic solvent can be used, for example, in amounts of 30 to 80% by weight, based on the halogenoformic ester of the formula (I).

It is an essential characteristic of the process according to the invention that the catalysts used are benzylalkyldimethylammonium halides. These can correspond, for example, to the formula (III)

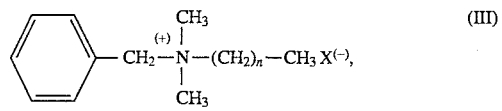

in which n represents an integer from 1 to 20, preferably 8 to 18, and

X represents a halogen, preferably chlorine.

The catalyst used can also be a mixture of different individuals of the formula (III).

The catalyst can be used, based on halogenoformic ester, for example in an amount of 0.001 to 0.1, preferably 0.005 to 0.05 mol %.

The process according to the invention can be carried out at atmospheric pressure, elevated pressure or low pressure. Atmospheric pressure is preferably employed.

The reaction temperature can be, for example, between −10° C. and the boiling temperature (at atmospheric pressure) of the halogenoformic ester used. It is preferably in the range 0° to 50° C. It is advantageous to stir vigorously while the process according to the invention is carried out.

The process according to the invention can be carried out both discontinuously and continuously. With the continuous procedure, residence times between 5 and 60 minutes can be employed, for example. With a discontinuous procedure, the reaction, depending on the size of the batch and the available cooling capacity, is generally completed after 10 minutes to 3 hours.

After the process according to the invention has been carried out, if appropriate after cooling and/or the addition of a sparing amount of water, a three-phase system is present, that is an organic phase which, in addition to the organic solvent, essentially contains the dialkyl dicarbonate prepared and, if appropriate, small amounts of unreacted halogenoformic ester, an aqueous phase which, in addition to water, contains the inorganic salts formed and an intermediate phase in which are situated the catalyst used and small amounts of the alcohol formed as a by-product from the halogenoformic ester used by ester saponification.

The reaction product can be isolated from the organic phase, e.g. by removal of the organic solvent by distillation. The organic solvent can if desired be recycled. The aqueous phase, with or without a preliminary purification, can be fed, for example, to a biological clarification stage for disposal.

It is a particular and surprising advantage of the process according to the invention that at the end of the reaction virtually all of the catalyst used is in the intermediate phase. The intermediate phase, in terms of volume, represents only a fraction of the aqueous and organic phase, for which reason it contains the catalyst used already in a highly enriched form. If required after addition of water, by distilling the intermediate phase separated off until pure water passes over, the starting products and volatile by-products contained in the intermediate phase can be separated off. The aqueous solution of the catalyst then remaining can without problem be recycled and reused as frequently as desired. The separation, recycling and/or disposal problems occurring in accordance with the prior art with the catalysts used there therefore do not occur with the process according to the invention. Moreover, with the catalysts to be used according to the invention, the reaction is to be carried out in a relatively short time.

EXAMPLES

Example 1

To 139.4 g of isobutyl chloroformate and 139.4 g of toluene was added dropwise within the course of 35 minutes a mixture of 290 g of 13.8% strength by weight aqueous sodium hydroxide solution and 3.3 g of benzyldodecyldimethylammonium chloride. By cooling, the reaction temperature was held between 30° and 40° C. After addition was completed and the stirrer turned off, the batch separated into three phases. The upper organic phase contained 105.2 g of diisobutyl dicarbonate (=96.5% of theory) and 0.32 g of isobutyl chloroformate. In the intermediate phase were situated the catalyst used and small amounts of isobutanol.

Example 2

To 100 g of methyl chloroformate and 100 g of toluene was added within the course of 30 minutes a mixture of 291.5 g of 13.8% strength by weight aqueous sodium hydroxide solution and 3.3 g of benzyldodecyldimethylammonium chloride. The reaction temperature was held by cooling at 10° and 15° C. After addition was completed and the stirrer turned off, 100 ml of water were added. The batch separated into three phases. In the top organic phase were situated 54.3 g of dimethyl dicarbonate (=85% of theory) and 4.6 g of methyl chloroformate. In the intermediate phase were situated the catalyst used and small amounts of methanol.

Example 3

Into a jacketed, cooled 60 ml continuous stirred reactor were fed, per hour, 240 ml of 13.5% strength by weight aqueous sodium hydroxide solution which contained 1.7% by weight of benzyl-($C_8$–$C_{18}$)-alkyldimethylammonium chloride and 278.4 ml of a 50% strength by weight isobutyl chloroformate/toluene solution. A residence time thus resulted of somewhat more than 7 minutes. The effluent reaction mixture was passed into a separator in which it separated into three phases. Per hour, in the upper organic phase 98.1 g of diisobutyl dicarbonate (98% of theory) and 7.14 g of unreacted isobutyl chloroformate were obtained. The intermediate phase was evaporated down to 80% of its volume and the remaining residue was used in a repetition of the example in which virtually the same results were obtained.

What is claimed is:

1. A process for the preparation of a dialkyl dicarbonate from the corresponding halogenoformic ester by reaction with alkali in the presence of a water-immiscible organic solvent and in the presence of a catalyst, which is a benzylalkyldimethylammonium halide, and wherein, upon completion of the reaction, the reaction mass is separated into three phases, the intermediate phase of which contains essentially all of the catalyst, the intermediate phase is separated off and, after separating off starting products and volatile products from the intermediate phase, the catalyst contained therein is separated off together with water and recycled.

2. The process of claim 1, in which a halogenoformic ester of the formula (I)

in which

Hal represents halogen, and

R represents a straight-chain or branched $C_1$–$C_{20}$-alkyl radical, is reacted with alkali while in the presence of a said catalyst whereby a dialkyl dicarbonate of the formula (II) is prepared

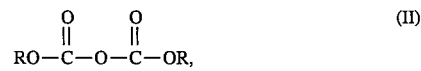

in which

R has the meaning given in formula (I).

3. The process of claim 1, in which the alkali used is an alkali metal hydroxide in the form of an aqueous solution.

4. The process of claim 1, in which the water-immiscible organic solvent used is an aromatic hydrocarbon, a chlorinated hydrocarbon or a water-immiscible ether.

5. The process of claim 1, in which the benzylalkyldimethylammonium halide used is one of the formula (III)

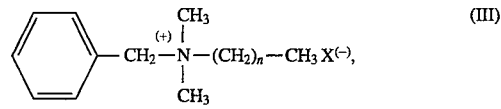

in which n represents an integer from 1 to 20 and

X represents a halogen.

6. The process of claim 1, in which benzylalkyldimethylammonium halide is used in an amount of 0.001 to 0.1 mol %, based on halogenoformic ester.

7. The process of claim 1, which is carried out at reaction temperatures between −10° C. and the boiling temperature (at atmospheric pressure) of the halogenoformic ester used.

* * * * *